(12) United States Patent
Nishioka (10) Patent No.: US 11,484,362 B2
(45) Date of Patent: Nov. 1, 2022

(54) MEDICAL INFORMATION PROCESSING APPARATUS AND MEDICAL INFORMATION PROCESSING METHOD

(71) Applicant: Canon Medical Systems Corporation, Otawara (JP)

(72) Inventor: Takahiko Nishioka, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1091 days.

(21) Appl. No.: 16/119,527

(22) Filed: Aug. 31, 2018

(65) Prior Publication Data

US 2019/0059999 A1 Feb. 28, 2019

(30) Foreign Application Priority Data

Aug. 31, 2017 (JP) .............................. JP2017-167657
Jul. 30, 2018 (JP) .............................. JP2018-142159

(51) Int. Cl.
 *A61B 34/10* (2016.01)
 *A61B 6/00* (2006.01)
 (Continued)

(52) U.S. Cl.
 CPC .............. *A61B 34/10* (2016.02); *A61B 6/032* (2013.01); *A61B 6/503* (2013.01); *A61B 6/5217* (2013.01); *A61B 8/0883* (2013.01); *A61B 8/5223* (2013.01); *A61B 90/37* (2016.02); *G16H 30/20* (2018.01); *G16H 50/50* (2018.01);
 (Continued)

(58) Field of Classification Search
 CPC ........ A61B 2034/105; A61B 2090/374; A61B 2090/3762; A61B 2090/378; A61B 34/10; A61B 5/021; A61B 5/1455; A61B 5/318; A61B 6/032; A61B 6/503; A61B 6/5217; A61B 8/0883; A61B 8/5223; A61B 90/37; G16H 30/20; G16H 50/50
 See application file for complete search history.

(56) References Cited

U.S. PATENT DOCUMENTS

2008/0177192 A1 7/2008 Chen et al.
2011/0245651 A1 10/2011 Nakamura
(Continued)

FOREIGN PATENT DOCUMENTS

| JP | 8-289877 | 11/1996 |
|----|----------|---------|
| JP | 2011-212043 | 10/2011 |
| JP | 2014-512201 | 5/2014 |

OTHER PUBLICATIONS

Office Action dated May 17, 2022, in corresponding Japanese Patent Application No. 2018-142159, 3 pages.

*Primary Examiner* — George Manuel
(74) *Attorney, Agent, or Firm* — Oblon, McClelland, Maier & Neustadt, L.L.P.

(57) ABSTRACT

A medical information processing apparatus according to an embodiment includes a memory storing a model that represents a relation between cell deformation and electric signal propagation; and processing circuitry configured to acquire four-dimensional image data acquired by imaging a three-dimensional structure of a cardiac muscle in time series, extract movement information on the cardiac muscle at multiple positions in the four-dimensional image data, and apply the model to the movement information with respect to the positions to calculate electric signal propagation at the positions.

20 Claims, 5 Drawing Sheets

(51) Int. Cl.
  *A61B 8/08* (2006.01)
  *A61B 90/00* (2016.01)
  *G16H 30/20* (2018.01)
  *G16H 50/50* (2018.01)
  *A61B 6/03* (2006.01)
  *A61B 5/1455* (2006.01)
  *A61B 5/021* (2006.01)
  *A61B 5/318* (2021.01)

(52) U.S. Cl.
  CPC ............. *A61B 5/021* (2013.01); *A61B 5/1455* (2013.01); *A61B 5/318* (2021.01); *A61B 2034/105* (2016.02); *A61B 2090/374* (2016.02); *A61B 2090/378* (2016.02); *A61B 2090/3762* (2016.02)

(56) References Cited

U.S. PATENT DOCUMENTS

| | | |
|---|---|---|
| 2014/0088943 A1 | 3/2014 | Trayanova et al. |
| 2014/0152653 A1* | 6/2014 | Dala-Krishna ....... G06T 7/0012 345/419 |

* cited by examiner

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2017-167657, filed on Aug. 31, 2017; and Japanese Patent Application No. 2018-142159, filed on Jul. 30, 2018, the entire contents of which are incorporated herein by reference.

FIELD

Embodiments described herein relate generally to a medical information processing apparatus and a medical information processing method.

BACKGROUND

The heart is an organ that contracts (gets excited) in accordance with propagated electric signals to deliver bloods inside the cardiac cavity to the entire body. Therefore, problems in propagation of electric signals cause abnormal cardiac rhythms such as tachycardia. Furthermore, for treatment of abnormal cardiac rhythms, doctors make treatment plans or perform surgery on the basis of information as to whether there is a problem in propagation of electric signals, which part of the heart causes a problem, or the like.

Here, as a conventional od for evaluating propagation of electric signals, there is a known method of recording changes in the electric potential inside the cardiac cavity by inserting an electrode catheter into the cardiac cavity. Furthermore, pacing stimulation is applied to the inside of the cardiac cavity to induce tachycardia so that the target site may be set, or the like, for diagnosis of abnormal cardiac rhythms or catheter ablation. However, this evaluation method imposes heavy loads on patients as an electrode catheter is inserted into the cardiac cavity or pacing stimulation is applied to induce tachycardia.

One of the methods for evaluating propagation of electric signals with few loads on patients is, for example, electrocardiograms. However, with electrocardiograms, although it may be determined whether propagation of an electric signal is faulty, it is difficult to identify an abnormal site. That is, electrocardiograms are sometimes not sufficient to diagnose abnormal cardiac rhythms or set the target site for catheter ablation.

DETAILED DESCRIPTION

A medical information processing apparatus comprises a memory and processing circuitry. The memory stores a model that represents a relation between cell deformation and electric signal propagation. The processing circuitry is configured to acquire four-dimensional image data acquired by imaging a three-dimensional structure of a cardiac muscle in time series, extract movement information on the cardiac muscle at multiple positions in the four-dimensional image data, and apply the model to the movement information with respect to the positions to calculate electric signal propagation at the positions.

With reference to the drawings, a detailed explanation is given below of an embodiment of the medical information processing apparatus and a medical information processing method.

First, a first embodiment is explained. In the first embodiment, a medical information processing system including a medical information processing apparatus and a medical image diagnostic apparatus is explained as an example. Furthermore, in the first embodiment, for example, an explanation is given of a case where propagation of an electric signal is calculated with regard to the cardiac muscle of a subject P1.

Figure 1:
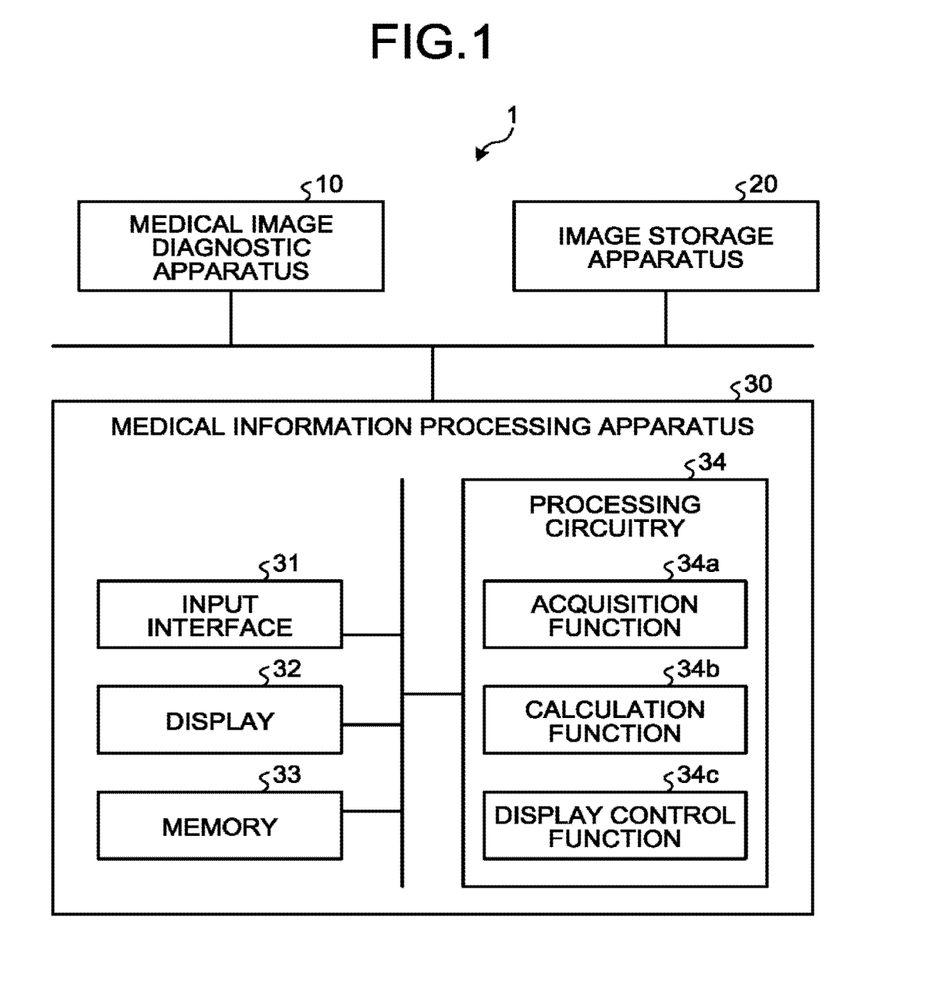
FIG. 1 is a block diagram that illustrates an example of the configuration of a medical information processing system according to a first embodiment.

As illustrated in FIG. 1, a medical information processing system 1 according to the first embodiment includes a medical image diagnostic apparatus 10, an image storage apparatus 20, and a medical information processing apparatus 30. Here, FIG. 1 is a block diagram that illustrates an example of the configuration of the medical information processing system 1 according to the first embodiment. As illustrated in FIG. 1, the medical image diagnostic apparatus 10, the image storage apparatus 20, and the medical information processing apparatus 30 are connected to one another via a network.

The medical image diagnostic apparatus 10 is an apparatus that acquires medical image data from the subject P1. For example, the medical image diagnostic apparatus 10 acquires four-dimensional image data (time-series three-dimensional image data) with regard to the cardiac muscle of the subject P1. Specifically, the medical image diagnostic apparatus 10 images the three-dimensional structure of the cardiac muscle of the subject P1 in time series, thereby acquiring four-dimensional image data. For example, the medical image diagnostic apparatus 10 is an X-ray CT (computed tomography) apparatus, MRI (magnetic resonance imaging) apparatus, ultrasound diagnostic apparatus, or like.

The image storage apparatus 20 is an apparatus that stores medical image data acquired by the medical image diagnostic apparatus 10. For example, the image storage apparatus 20 is implemented by using a computer device such as a server. According to the present embodiment, the image storage apparatus 20 acquires four-dimensional image data from the medical image diagnostic apparatus 10 via a network and stores the acquired four-dimensional image data in a memory provided inside or outside the apparatus.

The medical information processing apparatus 30 acquires four-dimensional image data via a network and performs various processes by using the acquired four-dimensional image data. For example, the medical information processing apparatus 30 is implemented by using a computer device such as workstation. According to the present embodiment, the medical information processing apparatus acquires four-dimensional image data from the medical image diagnostic apparatus 10 or the image storage apparatus 20 via a network. Furthermore, the medical information processing apparatus 30 calculates movement information on the cardiac muscle of the subject P1 on the basis of the acquired four-dimensional image data and calculates propagation (excitation propagation) of an electric signal in the cardiac muscle corresponding to the movement information.

As illustrated in FIG. 1, the medical information processing apparatus 30 includes an input interface 31, a display 32, a memory 33, and processing circuitry 34.

The input interface 31 receives various types of input operations from an operator, converts the received input operation into an electric signal, and outputs it to the processing circuitry 34. For example, the input interface 31 is implemented by using a mouse, keyboard, trackball, switch, button, joystick, touch panel, or the like.

The display 32 is a monitor that is viewed by an operator and, under the control of the processing circuitry 34, displays medical images as moving images or still images, displays propagation of electric signals calculated by the processing circuitry 34, and displays the GUI (graphical user interface) to receive various commands, various settings, and the like, from an operator via the input interface 31. For example, the display 32 is a liquid crystal display or a CRT (cathode ray tube) display.

The memory 33 is implemented by using, for example, a semiconductor memory device such as a RAM (random access memory) or a flash memory, a hard disk, or an optical disk. For example, the memory 33 stores four-dimensional image data acquired from the medical image diagnostic apparatus 10 or the image storage apparatus 20. Furthermore, the memory 33 stores a model that represents the relation between cell deformation and electric signal propagation. The model stored in the memory 33 described later. Furthermore, for example, the memory 33 stores programs for each circuitry included in the medical information processing apparatus 30 to perform their functions.

The processing circuitry 34 performs an acquisition function 34a, a calculation function 34b, and a display control function 34c, thereby controlling the overall operation of the medical information processing apparatus 30. For example, the processing circuitry 34 reads the program that corresponds to the acquisition function 34a from the memory 33 and executes acquire four-dimensional image data from the medical image diagnostic apparatus 10 or the image storage apparatus 20. Specifically, the acquisition function 34a acquires four-dimensional image data acquired by imaging the three-dimensional structure of the cardiac muscle in time series. Furthermore, the acquisition function 34a calculates movement information on the cardiac muscle of the subject P1 from the acquired four-dimensional image data. Specifically, the acquisition function 34a extracts movement information on the cardiac muscle at multiple positions in four-dimensional image data. Furthermore, for example, the processing circuitry 34 reads the program that corresponds to the calculation function 34b from the memory 33 and executes it to calculate electric signal propagation in the cardiac muscle of the subject P1 corresponding to the movement information. Specifically, the calculation function 34b applies a model representing the relation between cell deformation and electric signal propagation to movement information with respect to multiple positions in four-dimensional image data, thereby calculating electric signal propagation at multiple positions in four-dimensional image data. Furthermore, for example, the processing circuitry 34 reads the program that corresponds to the display control function 34c from the memory 33 and executes it to display electric signal propagation in the cardiac muscle of the subject P1 on the display 32. Specifically, the display control function 34c displays electric signal propagation at multiple positions in four-dimensional image data. Furthermore, calculation and display of electric signal propagation are described later.

In the medical information processing apparatus 30 illustrated in FIG. 1, each processing function is stored in the memory 33 in a form of program executable by a computer. The processing circuitry 34 is a processor that reads a program from the memory 33 and executes it to perform the function that corresponds to the program. In other words, after having read each program, the processing circuitry 34 has the function that corresponds to the read program. Here, in explanation of FIG. 1, the single processing circuitry 34 performs the acquisition function 34a, the calculation function 34b, and the display control function 34c; however, the processing circuitry 34 may be configured by combining multiple independent processors so that each processor executes a program to perform the function.

Figure 2:
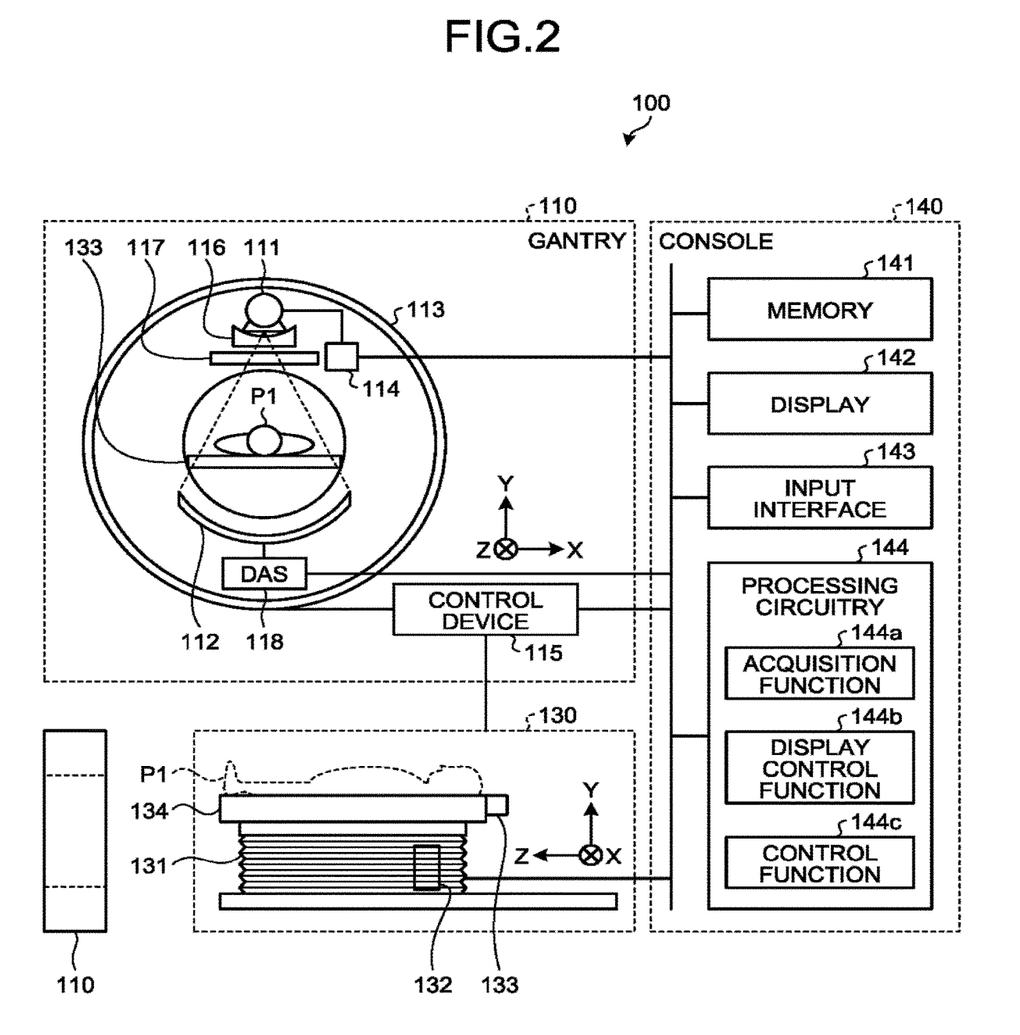
FIG. 2 is a block diagram that illustrates an example of the configuration of an X-ray CT apparatus according to the first embodiment.

Next, with reference to FIG. 2, a detailed explanation is given of the medical image diagnostic apparatus 10 that acquires four-dimensional image data. In FIG. 2, an X-ray CT apparatus 100 is explained as an example of the medical image diagnostic apparatus 10. FIG. 2 is a block diagram that illustrates an example of the configuration of the X-ray CT apparatus 100 according to the first embodiment.

As illustrated in FIG. 2, the X-ray CT apparatus 100 includes a gantry 110, a couch 130, and a console 140. Furthermore, the X-ray CT apparatus 100 is connected to an undepicted electrocardiograph. The electrocardiograph detects ECG (electrocardiogram) signals of the subject P1 via electrodes attached to the subject P1, generates an electrocardiogram, and transmits the generated electrocardiogram to the X-ray CT apparatus 100. Here, in FIG. 2, the Z-axis direction is the rotation axis of a rotation frame 113 when it is not tilted or the longitudinal direction of a tabletop 133 of the couch 130. Furthermore, the X-axis direction is the axis direction that is perpendicular to the 2-axis direction and that is horizontal to the floor surface. Moreover, the Y-axis direction is the axis direction that is perpendicular to the Z-axis direction and that is vertical to the floor surface.

The gantry 110 includes an X-ray tube 111, an X-ray detector 112, the rotation frame 113, an X-ray high-voltage device 114, a control device 115, a wedge 116, a collimator 117, and data acquisition circuitry 118.

The X-ray tube 111 is a vacuum tube that includes: a cathode (filament) that generates thermal electrons; and an anode (target) that generates X-rays after receiving collision of thermal electrons. The X-ray tube 111 uses a high voltage supplied from the X-ray high-voltage device 114 to emit thermal electrons from the cathode toward the anode, thereby generating X-rays.

The X-ray detector 112 detects X-rays that are emitted from the X-ray tube 111 and are passed through the subject P1 and outputs signals that correspond to the amount of detected X-rays to the data acquisition circuitry 118. The X-ray detector 112 includes for example multiple X-ray detecting element columns in which a plurality of X-ray detecting elements is arranged in a channel direction along a single circular arc with the focal point of the X-ray tube 111 at a center. The X-ray detector 112 has a configuration such that, for example, a plurality of X-ray detecting element columns with a plurality of X-ray detecting elements arranged in a channel direction is arranged in a slice direction (column direction, row direction). Furthermore, the X-ray detector 112 is, for example, an indirect-conversion type detector that includes a grid, a scintillator array, and an optical sensor array. The scintillator array includes a plurality of scintillators. The scintillator includes a scintillator crystal that outputs light with the photon quantity that corresponds to the amount of incident X-rays. The grid is located on the surface at the X-ray incident side of the scintillator array, and it includes an X-ray shielding plate that absorbs scattered X-rays. The optical sensor array has a function to convert electric signals in accordance with the amount of light from the scintillator and it includes, for example, an optical sensor such as a photomultiplier tube (photomultiplier: PMT). Furthermore, the X-ray detector 112 may be a direct-conversion type detector including a semiconductor device that converts incident X-rays into electric signals.

The rotation frame 113 is a circular frame that supports the X-ray tube 111 and the X-ray detector 112 such that they are opposed to each other and that rotates the X-ray tube 111 and the X-ray detector 112 through the control device 115. For example, the rotation frame is a cast that is made of aluminum. Furthermore, in addition to the X-ray tube 111 and the X-ray detector 112, the rotation frame 113 may also support the X-ray high-voltage device 114 and the data acquisition circuitry 118. Furthermore, the rotation frame 113 may also support various components that are not illustrated in FIG. 2. Hereafter, the rotation frame 113 and part that moves and rotates together with the rotation frame 113 in the gantry 110 are referred to as a rotary unit.

Furthermore, detection data generated by the data acquisition circuitry 118 is transmitted from a transmitter including a light emitting diode (LED) provided in the rotation frame 113 to a receiver including a photo diode provided in a non-rotary section of the gantry 110 through optical communications and is transferred to the console 140. Here, the non-rotary section is, for example, a fixed frame that rotatably supports the rotation frame 113. Furthermore, as the method for transmitting detection data from the rotation frame 113 to a non-rotary section in the gantry 110, any method may be used in addition to optical communications as long as it is non-contact type data transmission.

The X-ray high-voltage device 114 includes: a high-voltage generation device that includes electric circuits such as a transformer and a rectifier and generates a high voltage applied to the X-ray tube 111; and an X-ray control device that controls an output voltage in accordance with X-rays emitted from the X-ray tube 111. The high-voltage generation device may be a transformer type or an inverter type. Furthermore, the X-ray high-voltage device 114 may be provided in the rotation frame 113 or may be provided in an undepicted fixed frame.

The control device 115 includes driving mechanisms such as a motor and an actuator and circuitry that controls the mechanism. The control device 115 receives input signals from an input interface 143, an input interface provided in the gantry 110, or the like, and controls operation of the gantry 110 and the couch 130. For example, the control device 115 controls rotation of the rotation frame 113, tilt of the gantry 110, operation of the couch 130 and the tabletop 133, and the like. With regard to the control to tilt the gantry 110, for example, the control device 115 rotates the rotation frame 113 with the axis parallel to the X-axis direction at the center on the basis of input inclination angle (tilt angle) information. Furthermore, the control device 115 may be provided in the gantry 110 or may be provided in the console 140.

The wedge 116 is a filter for adjusting the amount of X-rays emitted from the X-ray tube 111. Specifically, the wedge 116 is a filter that transmits and attenuates X-rays emitted from the X-ray tube 111 so that X-rays emitted from the X-ray tube 111 to the subject P1 have a predetermined distribution. For example, the wedge 116 is a wedge filter or a bow-tie filter, and it is formed by processing aluminum, or the like, to have a predetermined target angle or a predetermined thickness.

The collimator 117 is a lead plate, or the like, which narrows down the irradiation range of X-rays that have transmitted through the wedge 116, and it forms slits by combining multiple lead plates, or the like. The numerical aperture and the position of the collimator 117 are adjusted by an undepicted collimator adjustment circuitry. Thus, the irradiation range of X-rays generated by the X-ray tube 111 is adjusted.

The data acquisition circuitry 118 is a DAS (data acquisition system). The data acquisition circuitry 118 includes: an amplifier that performs an amplification process on electric signals output from each X-ray detecting element of the X-ray detector 112; and an A/D converter that converts electric signals into digital signals, and it generates detection data. The data acquisition circuitry 118 is implemented by using, for example, a processor.

The couch 130 is an apparatus on which the P1, which is the target to be scanned, is placed and moved, and it includes a base 131, a couch driving device 132, the tabletop 133, and a support frame 134. The base 131 is a chassis that movably supports the support frame 134 in a vertical direction. The couch driving device 132 is a driving mechanism that moves the tabletop 133 on which the subject P1 is placed in the long axis direction of the tabletop 133, and it includes a motor, an actuator, and the like. The tabletop 133 provided on the top of the support frame 134 is a plate on which the subject P1 is placed. Furthermore, the couch driving device 132 may move the support frame 134 as well as the tabletop 133 in the long axis direction of the tabletop 133.

The console 140 includes a memory 141, a display 142, the input interface 143, and processing circuitry 144.

The memory 141 is implemented by using, for example, a semiconductor memory device such as a RAM or a flash memory, a hard disk, or an optical disk. For example, the memory 141 stores projection data, reconstruction image data, or electrocardiogram transmitted from the electrocardiograph. Furthermore, for example, the memory 141 stores programs for each circuitry included in the X-ray CT apparatus 100 to perform their functions.

The display 142 displays various types of information. For example, the display 142 displays four-dimensional image data generated by the processing circuitry 144 as moving images or still images and displays the GUI, or the like, for receiving various operations from an operator. For example, the display 142 is a liquid crystal display or a CRT display.

The input interface 143 receives various input operations from an operator, converts the received input operation into electric signals, and outputs them to the processing circuitry 144. For example, the input interface 143 receives a acquisition condition for acquiring projection data, a reconstruction condition for reconstructing CT image data, an image processing condition for generating four-dimensional image data from CT image data, and the like, from an operator. For example, the input interface 143 is implemented by using a mouse, keyboard, trackball, switch, button, joystick, or touch panel.

The processing circuitry 144 controls the overall operation of the X-ray CT apparatus 100. For example, the processing circuitry 144 includes an acquisition function 144a, a display control function 144b, and a control function 144c. The processing circuitry 144 is implemented by using for example a processor.

For example, the processing circuitry 144 reads the program that corresponds to the acquisition function 144a from the memory 141 and executes it to control the X-ray CT apparatus 100 so as to conduct scan. Here, the acquisition function 144a is capable of conducting scan by using various methods such as conventional scan, helical scan, or step-and-shoot methods.

Specifically, the acquisition function 144a controls couch driving device 132 so as to move the subject P1 into the imaging hole of the gantry 110. Furthermore, the acquisition function 144a controls the X-ray high-voltage device 114 so as to supply a high voltage to the X-ray tube 111. Furthermore, the acquisition function 144a adjusts the numerical aperture and the position of the collimator 117. Furthermore, the acquisition function 144a controls the control device 115 so as to rotate the rotary unit including the rotation frame 113. Moreover, the acquisition function 144a causes the data acquisition circuitry 118 to acquire projection data.

Furthermore, for example, the acquisition function 144a generates data by performing preprocessing, such as logarithmic conversion process, offset correction process, inter-channel sensitivity correction process, or beam hardening correction, on detection data output from the data acquisition circuitry 118. Here, data (detection data) before preprocessing is performed and data after preprocessing is performed are collectively referred to as projection data in some cases. Furthermore, for example, the acquisition function 144a generates CT image data. Specifically, the acquisition function 144a conducts a reconstruction process by using a filter-correction back projection technique, a successive approximation reconstruction technique, or the like, on projection data on which preprocessing has been conducted, thereby generating CT image data. Furthermore, the acquisition function 144a converts CT image data into three-dimensional image data in accordance with input operation, or the like, received from an operator via the input interface 143.

Here, the acquisition function 144a acquires the above-described three-dimensional image data in time series to acquire four-dimensional image data. For example, the acquisition function 144a acquires three-dimensional image data with respect to each of cardiac phases during cardiac systole of the subject P1 to acquire four-dimensional image data that represents contraction of the heart of the subject P1 in three dimensions. For example, the acquisition function 144a controls emission of X-rays on the basis of the electrocardiogram received from the electrocardiograph and acquires three-dimensional image data in synchronization with each of the cardiac phases during systole to acquire four-dimensional image data. Then, the acquisition function 144a stores four-dimensional image data in the memory 141 or transmits it to the image storage apparatus 20 or the medical information processing apparatus 30.

Furthermore, for example, the processing circuitry 144 reads the program that corresponds to the display control function 144b from the memory 141 and executes it to display four-dimensional image data on the display 142. Furthermore, for example, the processing circuitry 144 reads the program that corresponds to the control function 144c from the memory 141 and executes it to control various functions of the processing circuitry 144 in accordance with input operation received from an operator via the input interface 143.

In the X-ray CT apparatus 100 illustrated in FIG. each processing function is stored in the memory 141 in a form of program executable by a computer. The processing circuitry 144 is a processor that reads a program from the memory 141 and executes it to perform the function that corresponds to the program. In other words, after having read each program, the processing circuitry 144 has the function that corresponds to the read program. Here, in the case illustrated in FIG. 2, each processing function, i.e., the acquisition function 144a, the display control function 144b, and the control function 144c, are performed by using the single processing circuitry 144; however, this is not a limitation on embodiments. For example, the processing circuitry 144 may be configured by combining multiple independent processors so that each processor executes each program to perform each processing function. Furthermore, each processing function provided in the processing circuitry 144 may be performed by being distributed or combined in one or more processing circuits as appropriate.

The term "processor" used in the above explanation means, for example, a CPU (central processing unit), a GPU (graphics processing unit), or a circuit, such as an application specific integrated circuit (ASIC), a programmable logic device (e.g., a simple programmable logic device (SPLD), complex programmable logic device (CPLD), or a field programmable gate array (FPGA)). The processor reads a program stored in the memory 33 or the memory 141 and executes it, thereby implementing the function. Furthermore, instead of storing programs in the memory 33 or the memory 141, a configuration may be such that programs are directly installed in a circuit of a processor. In this case, the processor reads a program installed in the circuit and executes it, thereby implementing the function. Furthermore, with regard to each processor according to the present embodiment, each processor is not always configured as a single circuit but also configured as a single processor by combining multiple independent circuits so that its function is implemented.

An example of the configuration of the medical information processing system 1 is explained above. With this configuration, the medical information processing apparatus 30 in the medical information processing system 1 calculates propagation of an electric signal in the cardiac muscle of the subject P1 while loads on the subject P1 are reduced. Specifically, during a process of the processing circuitry 34 described later in detail, the medical information processing apparatus 30 acquires movement information based on four-dimensional image data on the cardiac muscle of the subject P1 and calculates propagation of an electric signal in the cardiac muscle corresponding to the movement information, thereby calculating propagation of an electric signal in the cardiac muscle of the subject P1 non-invasively. A detailed explanation is given below of process performed by the medical information processing apparatus 30 according to the first embodiment.

Figure 3:
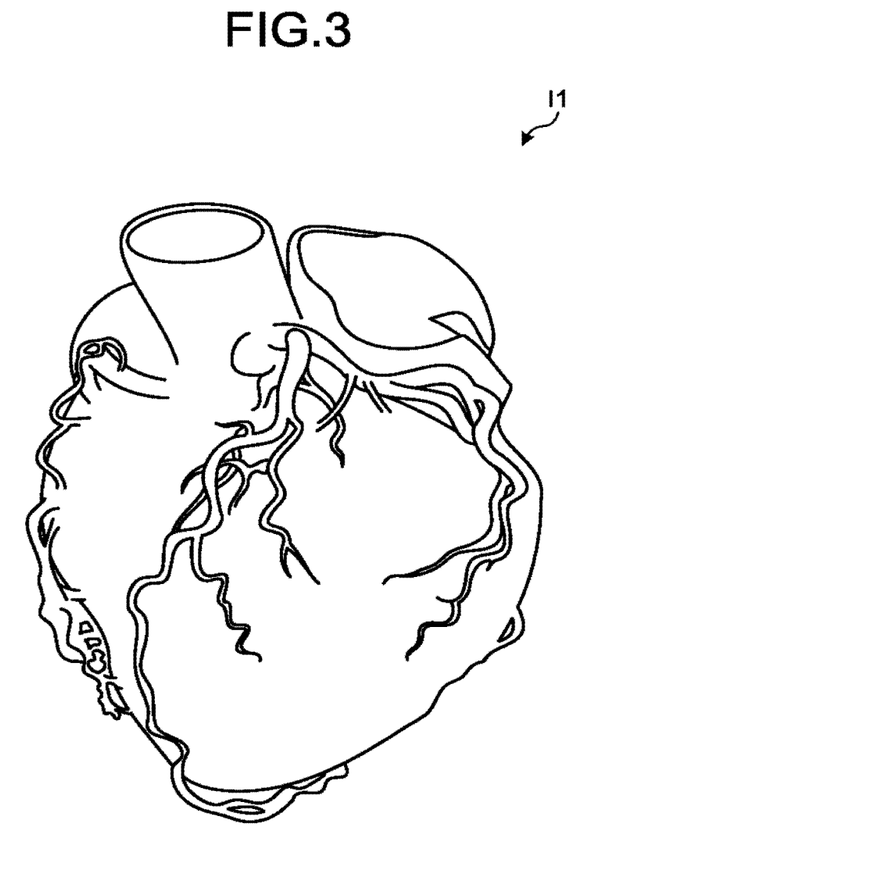
FIG. 3 is a diagram that illustrates an example of four-dimensional image data according to the first embodiment.

First, the acquisition function 34a acquires four-dimensional image data on the cardiac muscle of the subject P1 from the X-ray CT apparatus 100 or the image storage apparatus 10 and stores it in the memory 33. For example, the acquisition function 34a acquires four-dimensional image data I1 illustrated in FIG. 3 as the four-dimensional image data on the cardiac muscle of the subject P1 and stores it in the memory 33. Here, FIG. 3 is a diagram that illustrates an example of the our-dimensional image data I1 according to the first embodiment. Here, the four-dimensional image data I1 is a set of three-dimensional image data acquired in time series with regard to the cardiac muscle of the subject P1, and FIG. 3 illustrates one piece of three-dimensional image data included in the four-dimensional image data I1.

Next, the acquisition function 34a reads the four-dimensional image data I1 from the memory 33 and extracts movement information B1 on the cardiac muscle at multiple positions in the four-dimensional image data I1. Here, the movement information B1 is numerical data that relates, for example, the coordinates indicating each position of the cardiac muscle and the movement distance and the moving direction at each position of the cardiac muscle. Furthermore, the movement information B1 is image data where, for example, the movement distance and the moving direction at each position of the cardiac muscle are mapped.

For example, the acquisition function 34a first extracts an area (cardiac muscle area) that corresponds to the cardiac muscle from each of pieces of three-dimensional image data included in the four-dimensional image data I1. For example, the acquisition function 34a performs a segmentation process by using a region growing technique to extract an area where CT values are successive in space, a pattern matching technique using a shape template, or the like, on each piece of three-dimensional image data, thereby extracting a cardiac muscle area.

Then, the acquisition function 34a registrates cardiac muscle areas extracted from the respective pieces of three-dimensional image data with one another and calculates a relation of an anatomical position. Thus, the acquisition function 34a is capable of extracting the moving direction and the movement distance of an anatomical position as the movement information B1 while each piece of three-dimensional image data is acquired.

Figure 4:
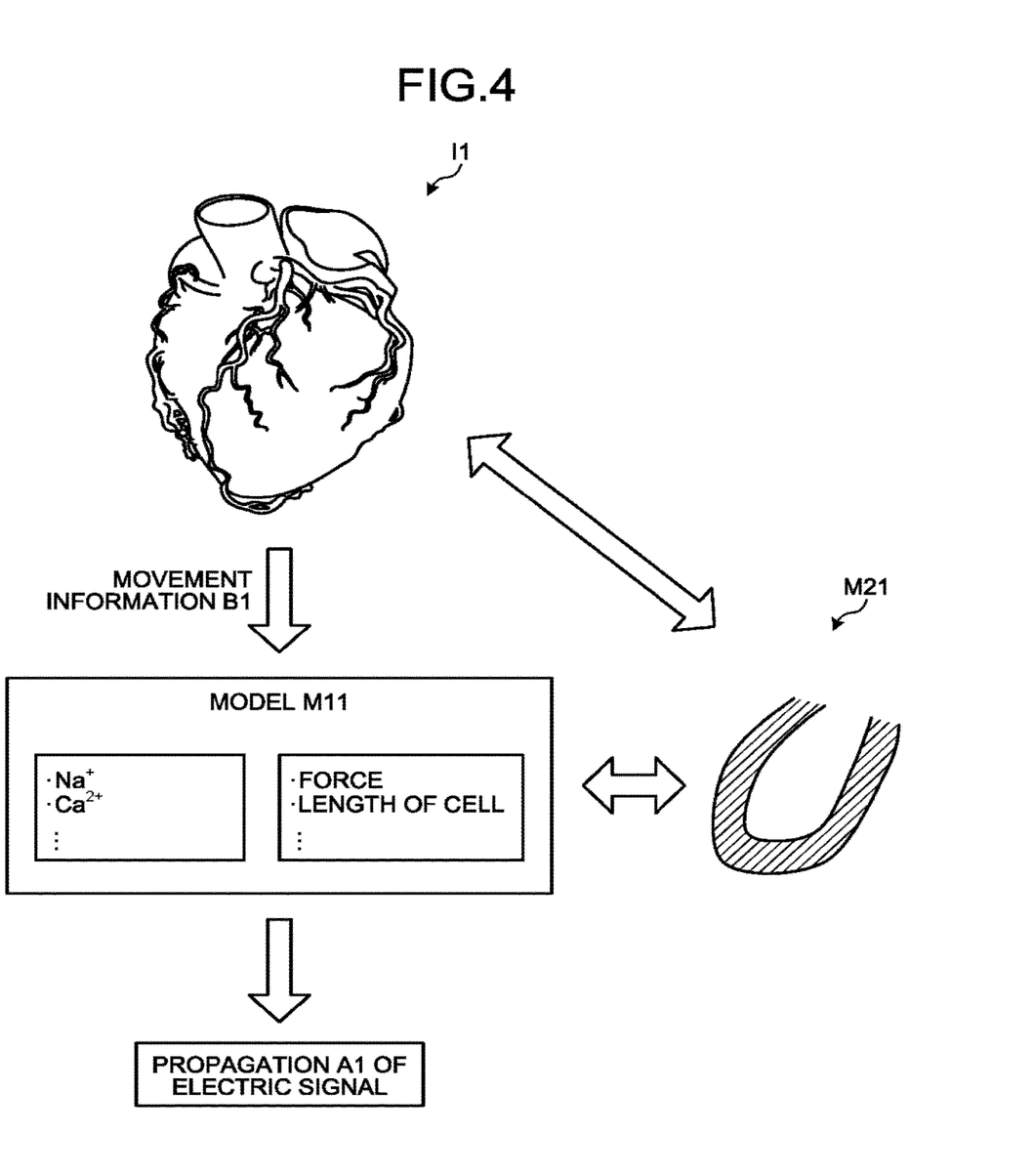
FIG. 4 is a diagram that illustrates an example of dynamic simulation of propagation of an electric signal and a muscle cell according to the first embodiment.

Then, the calculation function 34b uses a model M11 to conduct dynamic simulation on propagation of an electric signal and a muscle cell and calculates propagation A1 of an electric signal in the cardiac muscle of the subject P1 corresponding to the movement information B1. Here, with reference to FIG. 4, a detailed explanation is given of calculation of the propagation A1 of the electric signal by the calculation function 34b. FIG. 4 is a diagram that illustrates an example of dynamic simulation of propagation of an electric signal and a muscle cell according to the first embodiment.

For example, the calculation function 34b first reads the model M11 from the memory 33. Here, the model M11 is a model that represents the relation between cell deformation and electric signal propagation. For example, as illustrated in FIG. 4, the model M11 is a muscle cell model representing the electrophysiological relation between cell movement (time change in the force generated by a cell, the length of a cell, or the like) and an electric signal (ion concentration such as Na+ or Ca2+, or the like). Here, there may be a case where the memory 33 stores the model M11 that corresponds to the type of cell (e.g., proper cardiac muscle or specialized cardiac muscle). In this case, the calculation function 34b reads the one or more models M11 from the memory 33 in accordance with the type of cell included in the target site.

Then, as illustrated in FIG. 4, the calculation function 34b inputs the movement information B1 based on the four-dimensional image data I1 to the model M11 and calculates the propagation A1 of the electric signal in the cardiac muscle. That is, the calculation function 34b applies the model M11 to the movement information B1 with respect to multiple positions in the four-dimensional image data I1, thereby calculating the propagation A1 of the electric signal at multiple positions in the four-dimensional image data I1. Specifically, as illustrated in FIG. 4, the calculation function 34b first generates a cardiac muscle model M21 based on the four-dimensional image data I1. For example, the calculation function 34b generates shape data representing the shape of the cardiac muscle of the subject P1 on the basis of the cardiac muscle area extracted from the four-dimensional image data I1 and divides the generated shape data in accordance with the size and the shape of a muscle cell, thereby generating the cardiac muscle model M21. That is, the calculation function 34b generates the cardiac muscle model M21 as a set of muscle cells.

Then, with regard to an individual muscle cell in the cardiac muscle model M21, the calculation function 34b inputs the movement information B1 that corresponds to the position of the muscle cell to the model M11 as a time change in the force or the length of the cell, or the like. Thus, with regard to an individual muscle cell in the cardiac muscle model M21, the calculation function 34b calculates a time change in ion concentration corresponding to a time change in the input force or length of the cell, or the like. Furthermore, with regard to an individual muscle cell in the cardiac muscle model M21, the calculation function 34b calculates a time change in an electric signal corresponding to a time change in ion concentration, thereby calculating the propagation A1 of the electric signal in the cardiac muscle.

Here, the calculation function 34b may calculate the propagation A1 of an electric signal in consideration of continuity of the electric signal between muscle cells. Specifically, although an electric signal is sometimes interrupted, or the like, while it propagates between muscle cells, it flows with some continuity; therefore, the calculation function 34b may calculate the propagation A1 of an electric signal in the cardiac muscle while adjusting the electric signal in an individual muscle cell in the cardiac muscle model M21 so as to acquire continuity of the electric signal between muscle cells.

Furthermore, the calculation function 34b may calculate the propagation A1 of an electric signal within the range of part of the cardiac muscle or the entire cardiac muscle. For example, the calculation function 34b calculates the propagation A1 of an electric signal within the range that corresponds to a case of the subject P1. For instance, when the cardiac muscle of the subject P1 has a problem in propagating excitation, the calculation function 34b calculates, as the propagation A1 of an electric signal, a time change in the electric signal at each position inside the cardiac muscle and at each position on surfaces (the surface on the side of the cardiac cavity and the surface on the outer side) of the cardiac muscle. Thus, it is possible for the calculation function 34b to calculate faulty areas even when propagation of an electric signal is disturbed inside the cardiac muscle. Conversely, in a case that does not require observation on an electric signal inside the cardiac muscle, the calculation function 34b may calculate only a time change in an electric signal on the surface of the cardiac muscle at the side of the cardiac cavity as the propagation A1 of the electric signal.

As described above, the calculation function 34b conducts dynamic simulation of propagation of an electric signal and a muscle cell to calculate the propagation A1 of the electric signal. Here, the calculation function 34b may calculate the propagation A1 of an electric signal in consideration of the force received by a cell at each position of the cardiac muscle from a neighboring cell. This is because, although it is necessary to input the movement made by each cell due to an electric signal to the model M11 so as to properly calculate the electric signal, the movement information B1 based on the four-dimensional image data I1 contains both the movement made by each cell due to an electric signal and the movement due to pulling by a neighboring cell.

For example, the calculation function 34b uses the cardiac muscle model M21 based on the four-dimensional image data I1 to calculate the force received by a cell at each position of the cardiac muscle from a neighboring cell. For example, the calculation function 34b applies the Laplace model (the following Equation (1)) to a cell at each position of the cardiac muscle in the cardiac muscle model M21 to calculate the force received by a cell at each position of the cardiac muscle from a neighboring cell.

$$\Delta P = \frac{2T}{R} \quad (1)$$

In Equation (1), "ΔP" is a difference in pressure between inside and outside the cardiac muscle, "T" is a force (tensional force) received by a cell at each position of the cardiac muscle from a neighboring cell, and "R" is a curvature radius. For example, the calculation function 34b acquires the curvature radius R indicating the shape of the cardiac muscle based on the cardiac muscle model M21 with respect to each position of the cardiac muscle. Furthermore, the calculation function 34b acquires the pressure difference ΔP in accordance with the force acting on the cardiac muscle. For example, the calculation function 34b conducts analysis based on the blood pressure of the subject P1, thereby acquiring the pressure difference ΔP. For example, the calculation function 34b first determines whether each position of the cardiac muscle is located in any chamber (left atrium, left ventricle, right atrium, or right ventricle) of the heart. Then, the calculation function 34b acquires the reference value (e.g., the average value, or the like, of the pressures previously measured with regard to multiple persons) of the pressure in the determined chamber from the memory 33. Then, the calculation function 34b acquires the pressure difference ΔP by correcting the acquired reference value in accordance with the blood pressure of the subject P1. Furthermore, the calculation function 34b substitutes the curvature radius R and the pressure difference ΔP into Equation (1), thereby calculating the tensional force T.

Then, the calculation function 34b corrects the movement information B1 based on the four-dimensional image data I1 such that the effect of the calculated tensional force T is eliminated. In other words, the calculation function 34b subtracts a movement due to pulling by a neighboring cell from the movement information B1 based on the four-dimensional image data I1 to calculate the movement made by each cell due to the electric signal. Then, the calculation function 34b uses the model M11 to conduct dynamic simulation on propagation of the electric signal and a muscle cell, thereby calculating the propagation A1 of the electric signal in the cardiac muscle corresponding the corrected movement information B1 (movement made by each cell due to the electric signal).

Although an explanation is given above of case where the force received by a cell at each position of the cardiac muscle from a neighboring cell is calculated by using the Laplace model, this is not a limitation on embodiments. For example, the calculation function 34b may conduct structural analysis by using a numerical analysis method such as the finite element method (FEM) or the boundary element method to calculate the force received by a cell at each position of the cardiac muscle from a neighboring cell.

Furthermore, the calculation function 34b may calculate electric signal propagation by extracting a component of movement made by each cell in the cardiac muscle due to an electric signal from the movement information B1. This is because the movement information B1 based on the four-dimensional image data I1 contains a movement component due to oscillation of the entire heart relative to the subject P1 and a movement component in accordance with dilation and contraction of the heart due to bloods flowing in and out in addition to a movement made by each cell.

Specifically, the calculation function 34b first extracts a component of movement made by each cell in the cardiac muscle from the movement information B1. In other words, the calculation function 34b extracts movement information (hereafter, referred to as movement information B1') that corresponds to a component in the direction of the force generated by a cell at each position of the cardiac muscle from the movement information B1. The movement information B1' is an example of partial movement information.

For example, the calculation function 34b first acquires the fiber direction of a cell at each position of the cardiac muscle. Here, the calculation function 34b is capable of acquiring the fiber direction of a cell at each position of the cardiac muscle based on knowledge. For example, before the process to calculate electric signal propagation, the calculation function 34b acquires a three-dimensional model Mf representing the fiber direction of a cell at each position of the cardiac muscle and stores it in the memory 33. For example, the calculation function 34b generates the 3D model Mf by mapping a fiber direction on the typical heart to a three-dimensional model having the shape of the typical heart and stores it in the memory 33. Here, the calculation function 34b may acquire the 3D model Mf generated by a different apparatus other than the medical information processing apparatus 30 and store it in the memory 33. Then, the calculation function 34b deforms the 3D model Mf in accordance with the shape of the heart of the subject P1. For example, the calculation function 34b deforms the 3D model Mf such that its shape matches that of the cardiac muscle model M21 based on the four-dimensional image data I1. Then, the calculation function 34b assigns the fiber direction indicated by the deformed 3D model Mf to the heart of the subject P1, thereby acquiring the fiber direction of a cell at each position of the cardiac muscle. For example, the calculation function 34b assigns the fiber direction indicated by the deformed 3D model Mf to each position of the cardiac muscle model M21, thereby acquiring the fiber direction of a cell at each position of the cardiac muscle model M21. Here, cells of the cardiac muscle have characteristics such that they generate forces in their fiber directions. Therefore, the calculation function 34b is capable of extracting the movement information B1' that corresponds to a component in the direction of the force generated by a cell at each position of the cardiac muscle from the movement information B1 on the basis of the fiber direction of the cell. For example, the calculation function 34b resolves the movement information B1 into a component in the fiber direction of a cell and a component in other directions and extracts the component in the fiber direction of the cell as the movement information B1'.

According to another example, the calculation function 34b eliminates a component perpendicular to the curved surface of the cardiac muscle from the movement information B1, thereby extracting the movement information B1'. For example, the calculation function 34b first extracts the curved surface representing the shape of the cardiac muscle from the cardiac muscle model M21 based on the four-dimensional image data I1. Then, the calculation function 34b calculates the normal direction at each position of the extracted curved surface. Here, typically, cells of the cardiac muscle do not generate forces in a direction perpendicular to the curved surface of the cardiac muscle. Specifically, forces generated in a direction perpendicular to the cardiac wall from inside a cardiac chamber or atrium are typically caused by dilation and contraction of the heart due to bloods flowing in and out, and they are not generated by cells in the cardiac muscle. Therefore, the calculation function 34b eliminates a component perpendicular to the curved surface of the cardiac muscle from the movement information B1 so as to extract the Movement information B1' that corresponds to a component in the direction of the force generated by a cell at each position of the cardiac muscle. For example, the calculation function 34b resolves the movement information B1 into a component perpendicular to the curved surface of the cardiac muscle and components in other directions and extracts a component in other directions as the movement information B1'.

Then, the calculation function 34b uses the model M11 to conduct dynamic simulation of propagation of the electric signal and the muscle cell, thereby calculating the propagation A1 of the electric signal in the cardiac muscle corresponding to the movement information B1'. That is, the calculation function 34b applies the model M11 to the movement information B1' with respect to multiple positions in the four-dimensional image data I1, thereby calculating the propagation A1 of an electric signal at multiple positions in the four-dimensional image data I1. Here, by using the movement information B1', the calculation function 34b may improve the accuracy of the propagation A1 of the electric signal. That is, the calculation function 34b extracts a component of movement made by a cell in the cardiac muscle and conducts dynamic simulation, whereby the accuracy of the dynamic simulation may be improved. Furthermore, with regard to the movement information B1', correction may be made such that the effect of a force received by a cell at each position of the cardiac muscle from a neighboring cell is eliminated.

After the calculation function 34b calculates the propagation A1 of an electric signal, the display control function 34c displays the propagation A1 of the electric signal on the display 32. For example, on the display 32, the display control function 34c displays the four-dimensional image data I1 as a moving image or still image and displays the propagation A1 of an electric signal. Here, the display control function 34c may display the entire cardiac muscle included in the four-dimensional image data I1 or may display only an area where the propagation A1 of an electric signal is faulty.

For example, on the basis of the propagation A1 of an electric signal in the cardiac muscle, the display control function 34c first acquires the time (excitation start time) when an electric signal reaches each position of the cardiac muscle, the maximum excitation time when an electric signal reaches a maximum, duration of excitation, or the like. Then, on the display 32, the display control function 34c displays the four-dimensional image data I1 that is colored in accordance with the acquired excitation start time, maximum excitation time, duration, or the like.

According to another example, the display control function 34c first acquires the level (the maximal value, the average value, or the like) of the voltage at each position of the cardiac muscle on the basis of the propagation A1 of an electric signal in the cardiac muscle. Then, on the display 32, the display control function 34c displays the four-dimensional image data I1 that is colored in accordance with the acquired level of voltage.

According to another example, the display control function 34c first acquires a time change in the voltage at each position of the cardiac muscle on the basis of the propagation A1 of an electric signal in the cardiac muscle. Then, on the display 32, the display control function 34c displays the four-dimensional image data I1 as a moving image while representing the amount of change in the voltage in a color. Furthermore, for example, on the display 32, the display control function 34c displays a graph representing a time change in the voltage.

According to another example, the display control function 34c first acquires the propagation direction of an electric signal at each position of the cardiac muscle on the basis of the propagation A1 of the electric signal in the cardiac muscle. Then, on the display 32, the display control function 34c displays the four-dimensional image data I1 with the arrow (vector) indicating the propagation direction of the electric signal at each position of the cardiac muscle of the subject P1.

Furthermore, the display control function 34c may display the propagation A1 of the electric signal together with various types of information. For example, the acquisition function 34a further acquires time-series three-dimensional ultrasound image data that is acquired with regard to the heart of the subject P1. Then, the calculation function 34b calculates displacement at each position of the cardiac muscle from the time-series three-dimensional ultrasound image data. Then, the calculation function 34b differentiates the displacement at each position of the cardiac muscle to calculate a velocity. Furthermore, based on time changes in the velocity at each position of the cardiac muscle, the calculation function 34b calculates a strain curve that is a curve of time changes in a local strain of the cardiac muscle.

Then, the display control function 34c displays three-dimensional ultrasound image data based on the strain curve together with the propagation A1 of the electric signal. For example, the display control function 34c causes the display 32 to present the four-dimensional image data I1 that is colored in accordance with an excitation start time based on the propagation A1 of the electric signal and the three-dimensional ultrasound image data that is colored in accordance with the time when there is the largest strain. This allows the display control function 34c to provide an operator with more information about the movement of the heart of the subject P1.

Furthermore, strain curves based on three-dimensional ultrasound image data have many noises as they are affected by movements of neighboring cells and as they are acquired by differentiating displacement. However, the calculation function 34b resolves the movement information B1 based on the four-dimensional image data I1 into electric signals, whereby the accurate time when a local cell moves may be estimated with high accuracy. Furthermore, the display control function 34c displays the propagation A1 of the electric signal so that the time when each cell moves in the cardiac muscle may be displayed to an operator with high accuracy.

Furthermore, after the propagation A1 of the electric signal is calculated, the calculation function 34b may calculate movement information on the cardiac muscle based on the propagation A1 of the electric signal. Hereinafter, movement information on the cardiac muscle calculated based on the propagation A1 of the electric signal is referred to as movement information B2.

For example, the calculation function 34*b* calculates the movement information B2 that corresponds to the propagation A1 of the electric signal due to the process opposite to the process to calculate the propagation A1 of the electric signal corresponding to the movement information B1. Specifically, the calculation function 34*b* applies the model M11 to the movement information B1 to calculate the propagation A1 of the electric signal and then applies the model M11 to the propagation A1 of the electric signal to calculate the movement information B2.

After the calculation function 34*b* calculates the movement information B2, the display control function 34*c* displays the movement information B2 and the four-dimensional image data I1 on the display 32 comparably. For example, the display control function 34*c* sequentially deforms one piece of three-dimensional image data included in the four-dimensional image data I1 on the basis of the movement information B2, thereby generating four-dimensional image data I2 based on the movement information B2. Then, the display control function 34*c* displays the four-dimensional image data I1 and the four-dimensional image data I2 side by side.

By displaying the movement information B2 and the four-dimensional image data I1 comparably, the display control function 34*c* makes it possible to evaluate the calculated propagation A1 of the electric signal. That is, when the movement information B2 based on the propagation A1 of the electric signal matches the four-dimensional images data an operator may determine that the accuracy of the propagation A1 of the electric signal is reliable.

Moreover, the four-dimensional image data I1 contains components (a movement component due to oscillation of the entire heart or a movement component due to dilation and contraction of the heart) other than a movement made by each cell in the cardiac muscle due to an electric signal. Conversely, the movement information B2 based on the propagation A1 of the electric signal represents a movement made by each cell in the cardiac muscle. Therefore, by displaying the movement information B2 and the four-dimensional image data I1 comparably, the display control function 34*c* is capable of presenting an operator a difference due to the presence or absence of other components with regard to a movement in the cardiac muscle of the subject P1.

Figure 5:
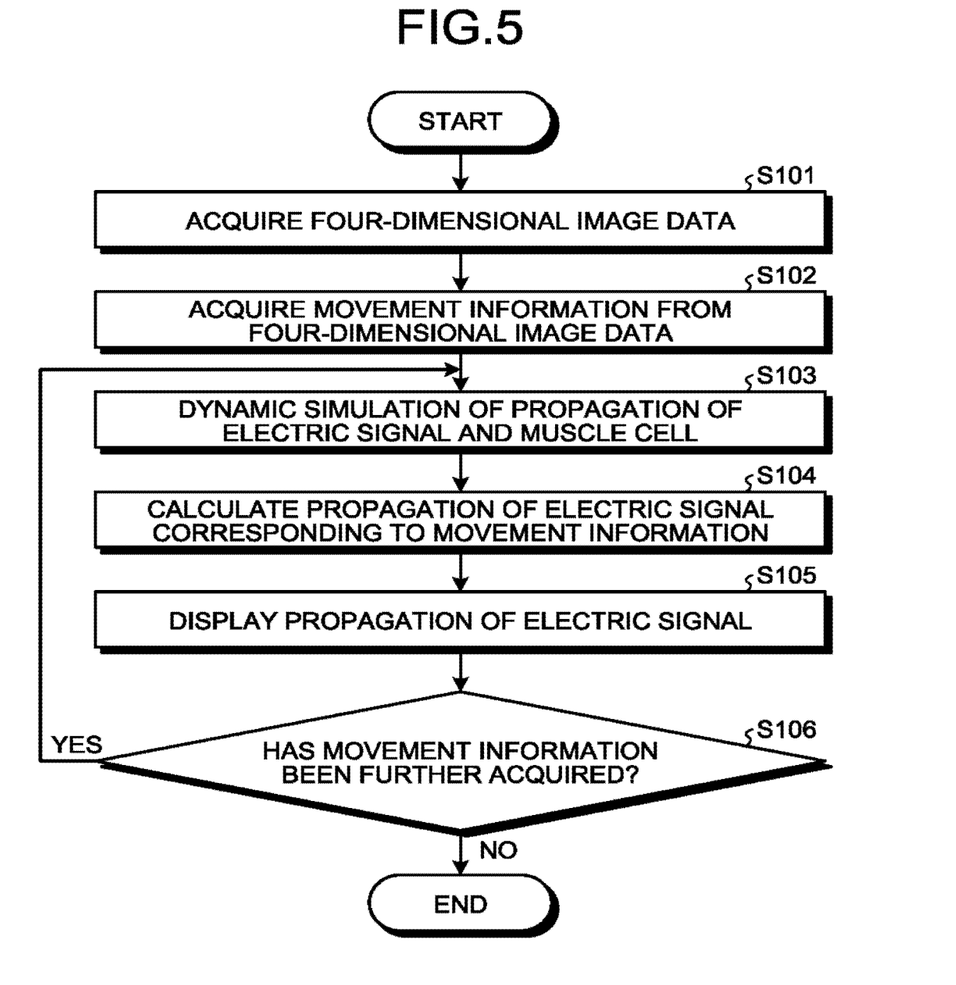
FIG. 5 is a flowchart that illustrates the sequential flow of a process of a medical information processing apparatus according to the first embodiment.

Next, with reference to FIG. 5, an explanation is given of an example of steps of a process performed by the medical information processing apparatus 30. FIG. 5 is a flowchart that illustrates the sequential flow process of the medical information processing apparatus 30 according to the first embodiment. Step S101, Step S102, and Step S106 are steps that correspond to the acquisition function 34*a*. Step S103 and Step S104 are steps that correspond to the calculation function 34*b*. Step S105 is a step that corresponds to the display control function 34*c*.

First, the processing circuitry 34 acquires the four-dimensional image data I1 on the cardiac muscle of the subject P1 from the X-ray CT apparatus 100 or the image storage apparatus 20 and stores it in the memory 33 (Step S101). Then, the processing circuitry 34 reads the four-dimensional image data I1 from the memory 33 and acquires the movement information B1 on the cardiac muscle of the subject P1 from the four-dimensional image data I1 (Step S102). Then, the processing circuitry 34 uses the model M11 to conduct dynamic simulation of propagation of an electric signal and a muscle cell (Step S103) and calculates the propagation A1 of the electric signal corresponding to the movement information B1 (Step S104). Then, the processing circuitry 34 displays the calculated propagation A1 of the electric signal on the display 32 (Step S105).

Here, the processing circuitry 34 determines whether the movement information B1 has been further acquired (Step S106). When the movement information B1 has been acquired (Step S106, Yes), the processing circuitry 34 proceeds to Step S103 again. Conversely, when the movement information B1 has not been acquired (Step S106, No), the processing circuitry 34 terminates the process.

As described above, according to the first embodiment, the acquisition function 34*a* acquires the movement information B1 on the cardiac muscle of the subject P1 based on the four-dimensional image data I1. The calculation function 34*b* uses the model M11 indicating the relation between the movement of a cell and an electric signal to calculate the propagation A1 of the electric signal in the cardiac muscle corresponding to the movement information B1. Therefore, the medical information processing apparatus 30 according to the first embodiment is capable of calculating propagation of an electric signal in the cardiac muscle non-invasively. For example, the medical information processing apparatus 30 is capable of calculating propagation of an electric signal without imposing loads on patients, such as directly applying stimulus to the heart of the subject P1 to induce tachycardia.

Furthermore, as described above, according to the first embodiment, the calculation function 34*b* further calculates the tensional force T, which is received by a cell from a neighboring cell, corrects the movement information B1 such that the effect of the tensional force T is eliminated, and calculates the propagation A1 of an electric signal corresponding to the corrected movement information B1. Therefore, the medical information processing apparatus 30 according to the first embodiment is capable of calculating propagation of an electric signal more properly in consideration of the state of the cardiac muscle. That is, the medical information processing apparatus 30 is capable of accurately calculating propagation of an electric signal as compared with a case where propagation of an electric signal is evaluated with a focus on only deformation of the cardiac muscle.

Furthermore, although an explanation is given of a case where the movement information B1 is acquired with respect to a single heartbeat, there may be a case where the acquisition function 34*a* acquires the movement information B1 with respect to multiple heartbeats. For example, first, the acquisition function 144*a* in the X-ray CT apparatus 100 controls emission of X-rays on the basis of electrocardiogram received from the electrocardiograph and acquires projection data in synchronization with each of cardiac phases. Then, the acquisition function 144*a* classifies projection data into projection data acquired with respect to a normal heartbeat (normal cardiac rhythm) and projection data acquired with respect to an abnormal heartbeat (abnormal cardiac rhythm). Here, the acquisition function 144*a* may conduct classification on the basis of electrocardiogram as to whether each piece of projection data is acquired with respect to a normal heartbeat or an abnormal heartbeat or may conduct classification on the basis of projection data itself.

Then, the acquisition function 144*a* generates three-dimensional image data with respect to each of the cardiac phases from the projection data acquired with regard to a normal heartbeat to acquire the four-dimensional image data I11. Furthermore, the acquisition function 144*a* generates three-dimensional image data with respect to each of the cardiac phases from the projection data acquired with regard to an abnormal heartbeat to acquire four-dimensional image data I12. Then, the acquisition function 144a stores the four-dimensional image data I11 acquired with respect to the normal heartbeat and the four-dimensional image data I12 acquired with respect to the abnormal heartbeat in the memory 141 or transmits them to the image storage apparatus 20 or the medical information processing apparatus 30. Here, the four-dimensional image data I11 and the four-dimensional image data I12 are examples of the four-dimensional image data I1.

Then, the acquisition function 34a acquires movement information B11 from the four-dimensional image data I11 acquired with respect to the normal heartbeat and acquires movement information B12 from the four-dimensional image data I12 acquired with respect to the abnormal heartbeat. That is, the acquisition function 34a acquires movement information for each of the heartbeats. Then, the calculation function 34b uses the model M11 to calculate propagation A11 of the electric signal corresponding to the movement information B11 and propagation A12 of the electric signal corresponding to the movement information B12. That is, the calculation function 34b calculates propagation of an electric signal for each heartbeat. Here, the movement information B11 and the movement information B12 are examples of the movement information B1, and the propagation A11 of the electric signal and the propagation A12 of the electric signal are examples of the propagation A1 of the electric signal.

Then, the display control function 34c displays the propagation A11 of the electric signal and the propagation A12 of the electric signal on the display 32 comparably. For example, the display control function 34c displays the propagation A11 of the electric signal and the propagation A12 of the electric signal side by side on the display 32 or displays them switchably. Thus, the medical information processing apparatus 30 displays the relation between a difference in heartbeats and propagation of an electric signal to support diagnosis. For example, the medical information processing apparatus 30 is capable of displaying a different part between the propagation A12 of the electric signal with respect to an abnormal heartbeat and the propagation A11 of the electric signal with respect to a normal heartbeat as a cause of the abnormal heartbeat.

Furthermore, although an explanation is given above of a case where the movement information B1 is acquired from the single subject P1, there may be a case where the acquisition function 34a acquires the movement information B1 from the multiple subjects P1. For example, first, the acquisition function 144a in the X-ray CT apparatus 100 acquires four-dimensional image data I13 on the cardiac muscle of a subject P11 who has no disease in the heart and four-dimensional image data I14 on the cardiac muscle of a subject P12 who has a disease in the heart. Then, the acquisition function 144a stores the four-dimensional image data I13 and the four-dimensional image data I14 in the memory 141 or transmits them to the image storage apparatus 20 or the medical information processing apparatus 30. Here, the subject P11 and the subject P12 are examples of the subject P1, and the four-dimensional image data I13 and the four-dimensional image data I14 are examples of the four-dimensional image data I1.

Then, the acquisition function 34a acquires movement information B13 from the four-dimensional image data I13 and movement information B14 from the four-dimensional image data I14. That is, the acquisition function 34a acquires movement information from the subjects P1. Then, the calculation function 34b uses the model M11 to calculate propagation A11 of the electric signal corresponding to the movement information B13 and propagation A14 of the electric signal corresponding to the movement information B14. That is, the calculation function 34b calculates propagation of an electric signal for each subject. Here, the movement information B13 and the movement information B14 are examples of the movement information B1, and the propagation A11 of the electric signal and the propagation A14 of the electric signal are examples of the propagation A1 of the electric signal.

Then, the display control function 34c displays the propagation A13 of the electric signal and the propagation A14 of the electric signal, calculated for each subject, on the display 32 comparably. For example, the display control function 34c displays the propagation A13 of the electric signal and the propagation A14 of the electric signal side by side on the display 32 or displays them switchably. Thus, the medical information processing apparatus 30 displays the relation between a difference in subjects and propagation of an electric signal to support diagnosis. For example, the medical information processing apparatus 30 is capable of displaying a different part between the propagation A14 of the electric signal of the subject P12 who has a disease in the heart and the propagation A13 of the electric signal of the subject P11 who has no disease in the heart as a cause of the abnormal heartbeat.

Furthermore, although an explanation is given above of a case where the four-dimensional image data I1 is acquired with regard to cardiac systole, there may be a case where the acquisition function 144a acquires the four-dimensional image data I1 corresponding to a single heartbeat including diastole. For example, when propagation of an electric signal occurs during other than systole due to a disease in the heart of the subject P1, or the like, the acquisition function 144a acquires the four-dimensional image data I1 corresponding to a single heartbeat. Then, the acquisition function 34a acquires the movement information B1 based on the four-dimensional image data I1 corresponding to a single heartbeat, and the calculation function 34b calculates the propagation A1 of the electric signal that corresponds to the movement information B1 corresponding to a single heartbeat.

In the above-described first embodiment, an explanation is given of a case where the model M11 stored in the memory 33 is directly used to calculate the propagation A1 of the electric signal in the cardiac muscle. Conversely, in a second embodiment, an explanation is given of a case where a model M12 that corresponds to the subject P1 is used to calculate the propagation A1 of the electric signal in the cardiac muscle.

The medical information processing apparatus according to the second embodiment has the same configuration as that of the medical information processing apparatus 30 according to the first embodiment illustrated in FIG. 1, but part of the process by the calculation function 34b is different. Therefore, a part having the same configuration as that described in the first embodiment is attached with the same reference numeral as that in FIG. 1, and explanation is omitted.

For example, the calculation function 34b first acquires at least one of ion concentration, blood pressure, and lesion distribution regarding the subject P1. For example, an operator first measures ion concentration of blood of the subject P1 by using an electrolyte measurement device. For example, the electrolyte measurement device may measure ion concentration by examining blood acquired from the subject P1 or may measure ion concentration on the basis of light emitted to a fingertip of the subject P1. Then, the calculation function 34b acquires ion concentration of the subject P1 after receiving input operation of ion concentration from an operator via the input interface 31.

Furthermore, for example, an operator measures the blood pressure of the subject P1 by using a blood-pressure measurement device. Then, the calculation function 34b acquires the blood pressure of the subject P1 by receiving input operation of the blood pressure from an operator via the input interface 31. Furthermore, for example, the calculation function 34b executes computer aided diagnosis (CAD) processing to detect a lesion area on the four-dimensional image data I1, thereby acquiring lesion distribution of the cardiac muscle of the subject P1.

Then, the calculation function 34b reads the model M11 from the memory 33 and deforms the model M11 in accordance with at least one of ion concentration, blood pressure, and lesion distribution of the subject P1 to generate the model M12 that corresponds to the subject P1. For example, in the heart of the subject P1 where cardiac infarction occurs, when a cardiac infarction portion (distribution of necrotic cells) is identified, the calculation function 34b generates the model M12 by assigning a muscle-cell model of the cardiac infarction to the cardiac infarction portion and assigning the same muscle-cell model as the model M11 to other than the cardiac infarction portion. Then, the calculation function 34b calculates the propagation A1 of the electric signal in the cardiac muscle by using the model M12 that corresponds to the subject P1.

An explanation is given above of a case where the model M12 is generated in accordance with a condition (a measured value of the ion concentration, a measured value of the blood pressure, lesion distribution due to CAD processing, or the like) acquired from the subject P1. However, this is not a limitation on embodiments, and there may be a case where the calculation function 34b generates the model M12 in accordance with a hypothetical condition.

For example, the acquisition function 34a first receives operation to set a lesion distribution regarding the cardiac muscle of the subject P1 from an operator via the input interface 31. Here, for example, an operator sets a lesion distribution by assuming a case where the lesion of the subject P1 is developed or a case where the lesion is removed during operation. Then, the calculation function 34b uses the model M12 that corresponds to the set lesion distribution to calculate the propagation A1 of the electric signal in the cardiac muscle. Then, the display control function 34c displays the calculated propagation A1 of the electric signal on the display 32. For example, the display control function 34c displays the propagation A1 of the electric signal calculated by using the model M12 that corresponds to the lesion distribution due to CAD processing and the propagation A1 of the electric signal calculated by using the model M12 that corresponds to the lesion distribution set by an operator on the display 32 comparably.

As described above, according to the second embodiment, the calculation function 34b uses the model M12 that corresponds to the subject P1 to calculate the propagation A1 of an electric signal in the cardiac muscle. Therefore, the medical information processing apparatus 30 according to the second embodiment is capable of calculating propagation of an electric signal in the cardiac muscle more correctly by using individual information on the subject P1.

Furthermore, as described above, according to the second embodiment, the calculation function 34b uses the model M12 that corresponds to the set lesion distribution to calculate the propagation A1 of an electric signal in the cardiac muscle. Therefore, the medical information processing apparatus 33 according to the second embodiment is capable of supporting diagnosis by calculating not only propagation of an electric signal in the subject P1 at present but also propagation of an electric signal after catheter ablation is performed, propagation of an electric signal when a lesion is developed without performing catheter ablation, or the like.

Although the first and the second embodiments are explained above, various different embodiments may be implemented other than the above-described embodiments.

For example, the calculation function 34b may further use an electrocardiogram to calculate the propagation A1 of an electric signal. For example, the calculation function 34b calculates the propagation A1 of the electric signal in the cardiac muscle of the subject P1 such that it is related to propagation A2 of the electric signal indicated by the electrocardiogram of the subject P1.

Specifically, the acquisition function 34a first acquires an electrocardiogram of the subject P1. Here, there may be a case where the acquisition function 34a acquires an electrocardiogram that is measured during scan to acquire the four-dimensional image data I1, or there may be a case where it acquires an electrocardiogram that is measured before or after scan.

Then, the calculation function 34b calculates the propagation A2 of the electric signal in the cardiac muscle of the subject P1 on the basis of the electrocardiogram. For example, the calculation function 34b identifies time intervals that correspond to the P wave and the QRS wave from the waveform of an electrocardiogram. Here, the calculation function 34b acquires the start time of the P wave as the time when an electric signal occurs in the sinus node. Furthermore, the calculation function 34b acquires ⅔ of the time interval corresponding to the P wave after its start as the time when the electric signal propagates through the right atrium. Furthermore, the calculation function 34b acquires ⅔ time interval corresponding to the P wave before its end as the time when the electric signal propagates through the left atrium. Moreover, the calculation function 34b acquires the time interval corresponding to the QRS wave as the time when an electric signal propagates through the bundle of His or the left leg/right leg.

Furthermore, the calculation function 34b uses the model M11 or the model M12 to calculate the propagation A1 of the electric signal in the cardiac muscle corresponding to the movement information B1. Furthermore, the calculation function 34b compares the calculated propagation A1 of the electric signal and the propagation A2 of the electric signal indicated by the electrocardiogram. Here, when the difference between the propagation A1 of the electric signal and the propagation A2 of the electric signal is small, the calculation function 34b terminates the process.

Conversely, when the difference between the propagation A1 of the electric signal and the propagation A2 of the electric signal is more than a threshold, the calculation function 34b corrects the propagation A1 of the electric signal. For example, when the value indicated by the propagation A1 of the electric signal is significantly large relative to the value indicated by the propagation A2 of the electric signal with regard to the time from when an electric signal occurs in sinus node to when propagation of the electric signal starts in the right atrium, the calculation function 34b corrects the propagation A1 of the electric signal to shorten the time from when an electric signal occurs in the sinus node to when propagation of the electric signal starts in the right atrium.

Then, the calculation function 34b uses the model M11 or the model M12 to calculate movement information B3 on the cardiac muscle corresponding to the corrected propagation A1 of the electric signal. Specifically, the calculation function 34b calculates the movement information B3 corresponding to the propagation A1 of the electric signal during the process that is opposite to the process to calculate the propagation A1 of the electric signal corresponding to the movement information B1. Then, the calculation function 34b compares the movement information B1 and the movement information B3.

Here, when the difference between the movement information B1 and the movement information B3 is small, the calculation function 34b terminates the process. Conversely, when the difference between the movement information B1 and the movement information B3 is more than the threshold, the calculation function 34b corrects the movement information B1. Then, the calculation function 34b calculates the propagation A1 of the electric signal in the cardiac muscle corresponding to the corrected movement information B1. Furthermore, the calculation function 34b repeatedly compares the propagation A1 of the electric signal with the propagation A2 of the electric signal and the movement information B1 with the movement information B3, as described above, a predetermined number of times or until the difference become less than the threshold. This allows the calculation function 34b to improve accuracy of the propagation A1 of the electric signal corresponding to the movement information B1 on the basis of the electrocardiogram.

Furthermore, after the propagation A1 of the electric signal is calculated, the calculation function 34b may determine whether the propagation A1 of the electric signal satisfies a constraint condition. Specifically, the calculation function 34b may determine whether the calculated propagation A1 of the electric signal can actually occur.

For example, there is a limit on the velocity at which electric signals propagate through the cardiac muscle of the subject P1, and electric signals do not propagate at a velocity more than this limit. Furthermore, for example, electric signals propagate continuously, and electric signals do not propagate switchably. Therefore, the calculation function 34b determines whether the propagation A1 of an electric signal at multiple positions in the four-dimensional image data I1 satisfies a constraint condition with regard to at least one of the velocity and the continuity of electric signal propagation in the cardiac muscle.

Here, when the propagation A1 of the electric signal does not satisfy a constraint condition, for example, the calculation function 34b recalculates the propagation A1 of the electric signal at multiple positions in the four-dimensional image data I1. Here, the calculation function 34b may change a calculation condition to recalculate the propagation A1 of the electric signal. For example, the calculation function 34b changes a model or movement information to be used to recalculate the propagation A1 of the electric signal. For instance, when the propagation A1 of the electric signal has been calculated by using the model M11, the calculation function 34b uses the model M12 to recalculate the propagation A1 of the electric signal. According to another example, when the propagation A1 of the electric signal has been calculated by using the movement information B1, the calculation function 34b uses the movement information B1' to recalculate the propagation A1 of the electric signal.

Alternatively, the calculation function 34b may exclude part that does not satisfy a constraint condition, included in the propagation A1 of the electric signal. Specifically, the calculation function 34b may remove part that does not satisfy a constraint condition, included in the calculated propagation A1 of the electric signal, to acquire the final result. In this case, the display control function 34c displays part other than the part that does not satisfy the constraint condition, included in the propagation A1 of the electric signal. Alternatively, the display control function 34c displays the propagation A1 of the electric signal in the form that makes it possible to recognize that the propagation A1 of the electric signal includes part that does not satisfy the constraint condition. For example, the display control function 34c displays the propagation A1 of the electric signal such that part that does not satisfy the constraint condition, included in the propagation A1 of the electric signal, is colored in black.

Furthermore, in explanation according to the above-described embodiment, the processing circuitry 34 of the medical information processing apparatus 30 includes the acquisition function 34a and the calculation function 34b. However, this is not a limitation on embodiments. For example, there may be a case where the processing circuitry 144 of the X-ray CT apparatus 100 has a function that corresponds to the acquisition function 34a and the calculation function 34b (hereafter, referred to as an acquisition function 144d and a calculation function 144e).

In this case, the acquisition function 144a first acquires the four-dimensional image data I1 on the cardiac muscle of the subject P1. Then, the acquisition function 144d acquires the movement information B1 on the cardiac muscle of the subject P1 from the four-dimensional image data I1. Then, the calculation function 144e uses the model M11 or the model M12 to calculate the propagation A1 of the electric signal in the cardiac muscle corresponding to the movement information B1. Then, the display control function 144b displays the calculated propagation A1 of the electric signal on the display 142.

Furthermore, according to the above-described embodiment, an explanation is given of a case where the acquisition function 34a of the medical information processing apparatus 30 calculates movement information from the four-dimensional image data I1. However, this is not a limitation on embodiments. For example, there may be a case where the acquisition function 144d of the X-ray CT apparatus 100 calculates the movement information B1 on the cardiac muscle of the subject P1 from the four-dimensional image data I1 and the acquisition function 34a acquires the movement information B1 from the X-ray CT apparatus 100.

Furthermore, in the above-described embodiment, an explanation is given of a case where the propagation A1 of the electric signal is calculated with respect to the cardiac muscle of the subject P1. However, this is not a limitation on embodiments. For example, the acquisition function 34a may set a muscle other than the cardiac muscle as the target site and acquire movement information based on four-dimensional image data on the target site. Furthermore, the calculation function 34b uses the model M11 to calculate propagation of an electric signal in the target site corresponding to the movement information.

Furthermore, in the above-described embodiment, an explanation is given of a case where the propagation A1 of the electric signal is calculated by using the model M11 or the model M12. However, this is not a limitation on embodiments. For example, there may be a case where the calculation function 34b reads the database that defines the correspondence relation between the movement information B1 and the propagation A1 of the electric signal from the memory 33 and compares the movement information B1 acquired by the acquisition function 34a with the database to calculate the propagation A1 of the electric signal.

Components of each apparatus according to the above-described embodiment are functionally conceptual and do not necessarily need to be physically configured as illustrated in the drawings. Specifically, specific forms of separation and combination of each apparatus are not limited to those depicted in the drawings, and a configuration may be such that all or some of them are functionally or physically separated or combined in an arbitrary unit depending on various types of loads usage. Furthermore, all or any of various processing functions performed by each apparatus may be implemented by a CPU and a program analyzed and executed by the CPU or may be implemented by wired logic hardware.

Furthermore, the medical information processing method described in the above-described embodiment may be performed when a prepared program is performed by a computer such as a personal computer or workstation. The program may be distributed via a network such as the Internet. Furthermore, the program may be executed by being recorded in a recording medium readable by a computer, such as hard disk, flexible disk (FD), CD-ROM, MO, or DVD, and being read by the computer from the recording medium.

According to at least one of the above-described embodiments, propagation of an electric signal is calculable while loads on a patient are reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
a memory storing a model that represents a relation between cell deformation and electric signal propagation and is used to calculate the electric signal propagation based on the cell deformation; and
processing circuitry configured to
acquire four-dimensional image data acquired by imaging a three-dimensional structure of a cardiac muscle in time series,
extract movement information on the cardiac muscle at multiple positions in the four-dimensional image data, and
apply the model to the movement information with respect to the positions to calculate electric signal propagation at the positions.

2. The medical information processing apparatus according to claim 1, wherein the processing circuitry further calculates a force received by a cell at each position of the cardiac muscle from a neighboring cell, corrects the movement information such that an effect of the force is eliminated, and applies the model to the movement information corrected with respect to the positions to calculate electric signal propagation at the positions.

3. The medical information processing apparatus according to claim 2, wherein the processing circuitry calculates a force received by a cell at each position of the cardiac muscle from a neighboring cell in accordance with a shape of the cardiac muscle and a force applied to the cardiac muscle.

4. The medical information processing apparatus according to claim 1, wherein the processing circuitry extracts partial movement information corresponding to a component in a direction of a force generated by a cell at each position of the cardiac muscle from the movement information and applies the model to the partial movement information with respect to the positions to calculate electric signal propagation at the positions.

5. The medical information processing apparatus according to claim 4, wherein the processing circuitry extracts the partial movement information based on a fiber direction of a cell at each position of the cardiac muscle.

6. The medical information processing apparatus according to claim 4, wherein the processing circuitry eliminates a component perpendicular to a curved surface of the cardiac muscle from the movement information, thereby extracting the partial movement information.

7. The medical information processing apparatus according to claim 1, wherein the processing circuitry
further acquires an electrocardiogram of a subject, and
calculates electric signal propagation at the positions as being related to propagation of an electric signal indicated by the electrocardiogram.

8. The medical information processing apparatus according to claim 1, wherein the processing circuitry determines whether electric signal propagation calculated at the positions satisfies a constraint condition with regard to at least one of a velocity and a continuity of electric signal propagation in the cardiac muscle and, when the constraint condition is not satisfied, recalculates electric signal propagation at the positions.

9. The medical information processing apparatus according to claim 1, wherein the processing circuitry excludes part that does not satisfy a constraint condition, included in electric signal propagation calculated at the positions, with regard to at least one of a velocity and a continuity of electric signal propagation in the cardiac muscle.

10. The medical information processing apparatus according to claim 1, wherein the processing circuitry uses the model corresponding to a subject to calculate electric signal propagation at the positions.

11. The medical information processing apparatus according to claim 10, wherein the processing circuitry uses the model corresponding to ion concentration of a subject to calculate electric signal propagation at the positions.

12. The medical information processing apparatus according to claim 10, wherein the processing circuitry uses the model corresponding to a blood pressure of a subject to calculate electric signal propagation at the positions.

13. The medical information processing apparatus according to claim 10, wherein the processing circuitry uses the model corresponding to a lesion distribution of the cardiac muscle to calculate electric signal propagation at the positions.

14. The medical information processing apparatus according to claim 13, wherein the processing circuitry
calculates movement information on the cardiac muscle based on electric signal propagation calculated at the positions, and
displays the movement information calculated and the four-dimensional image data comparably.

15. The medical information processing apparatus according to claim 1, wherein the processing circuitry further receives an operation to set a lesion distribution in the cardiac muscle, and uses the model corresponding to the lesion distribution to calculate electric signal propagation at the positions.

16. The medical information processing apparatus according to claim 1, wherein the processing circuitry extracts the movement information with regard to multiple heartbeats, and calculates electric signal propagation at the positions with respect to each heartbeat.

17. The medical information processing apparatus according to claim 1, wherein the processing circuitry further displays electric signal propagation calculated at the positions.

18. The medical information processing apparatus according to claim 16, wherein the processing circuitry extracts the movement information from multiple subjects, calculates electric signal propagation at the positions with regard to each subject, and displays electric signal propagation at the positions, calculated with respect to each subject comparably.

19. A medical information processing apparatus comprising processing circuitry configured to acquire movement information on a target site at multiple positions in four-dimensional image data on the target site, and apply a model wherein the model represents a relation between cell deformation and electric signal propagation and is used to calculate the electric signal propagation based on the cell deformation to the movement information with respect to the positions to calculate electric signal propagation at the positions.

20. A medical information processing method comprising:

acquiring four-dimensional image data acquired by imaging a three-dimensional structure of a cardiac muscle in time series, extracting movement information on the cardiac muscle at multiple positions in the four-dimensional image data, and applying a model wherein the model represents a relation between cell deformation and electric signal propagation and is used to calculate the electric signal propagation based on the cell deformation to the movement information with respect to the positions to calculate electric signal propagation at the positions.

* * * * *